US006114160A

United States Patent [19]
Croteau et al.

[11] Patent Number: 6,114,160
[45] Date of Patent: Sep. 5, 2000

[54] COMPOSITIONS AND METHODS FOR TAXOL BIOSYNTHESIS

[75] Inventors: Rodney B. Croteau, Pullman; Mark R. Wildung, Colfax, both of Wash.

[73] Assignee: Washington State University Research Foundation, Pullman, Wash.

[21] Appl. No.: 09/315,861

[22] Filed: May 20, 1999

Related U.S. Application Data

[62] Division of application No. 08/843,363, Apr. 15, 1997, Pat. No. 5,994,114.
[60] Provisional application No. 60/015,993, Apr. 15, 1996.

[51] Int. Cl.[7] .............................. C12N 9/88; C12N 1/20; C12N 15/00; C07H 21/04
[52] U.S. Cl. ..................... 435/232; 435/69.1; 435/252.3; 435/320.1; 435/419; 435/183; 435/254.11; 800/295; 536/23.2; 536/24.3
[58] Field of Search .................................. 435/232, 69.1, 435/252.3, 320.1, 419, 183, 254.11; 800/295; 536/23.2, 24.3

[56] References Cited

PUBLICATIONS

Hezari et al. (Oct. 1995) Arch. Biochem. Biophys. 322 (2) : 437–444.
Bensen et al., "Cloning and characterization of the Maize An1 Gene," *Plant Cell* 7:75–84 (1995).
Cane et al., "Pentalenene Synthase. Purification, Molecular Cloning, Sequencing, and High–Level Expression in *Escherichia coli* of a Terpenoid Cyclase from Streptomyces UC5319," *Biochem*.33:5846–5857 (1997).
Cane et al., "Trichodiene Synthase. Idenification of Active Site Residues by Site–Directed Mutagensis," *Biochem.* 34:2480–2488 (1995).
Chappell, Joseph, "Biochemistry and Molecular Biology of the Isoprenoid Biosynthetic Pathway in Plants," *Ann. Rev. Plant Physiol. Plant Mol. Biol.* 46:521–547 (1995).
Chen et al., "Isoprenyl Diphosphate Synthases: Protein Sequence comparisons, a Phylogenetic Tree, and Predictions of Secondary Structure," *Protein Sci.* 3:600–607 (1994).
Colby et al., "4S–Limonene Synthase from the Oil Glands of Spearment (*Menta spicata*)," *J. Biol. Chem.* 268:23016–23024 (1993).
Croteau et al., in Taxane Anticancer Agents: Basic Science and Current Status, George at al. (eds.), pp. 72–80, American Chemical Society, Washington, DC (1995).
Facchini et al.,"Gene family for an Elicitor–Induced Sesquiterpene Cyclase in Tobacco," *Proc. Natl. Acad. Sci. USA* 89:11088–11092 (1992).
Floss et al., in Taxol: Science and Applications, Suffness (ed.), pp. 191–208, CRC Press, Boca Raton, FL (1995).
Hezari et al., "Purification and Characterization of Taxa–4(5), 11(12)–diene Synthase from Pacific Yew (*Taxus brevifolia*) that Catalyzes the First Committed Step of Taxol Bosynthesis," *Arch. Biochem. Biophys.* 322:437–444 (1995).
Hezari et al., "Taxol Biosynthesis: An Update," *Planta Med.* 63:291–295 (1997).
Hezari et al., "Taxol Production and Taxadiene Synthase Activity in *Taxus canadensis* Cell Suspension Cultures," *Arch. Biochem. Biophy.* 337:185–190 (1997).

Koepp et al., "Cyclization of Geranylgeranyl Disphosphate to Taxa–4(5), 11(12)–diene Is the Committed Step of Taxol Biosynthesis in Pacific Yew," *J. Biol. Chem.* 270:8686–8690 (1995).
LaFever et al., "Diterpenoid Resin Acid Biosynthesis in Conifers: Enzymatic Cyclization of Geranylgeranyl Pyrophosphate to Abietadiene, the Precursor of Abietic Acid," *Arch. Biochem. Biophys.* 313:139–149 (1994).
Lin et al., "Mechanism of Taxadiene Synthase, a Diterpene Cyclase that Catalyzes the First Step to Taxol Biosynthesis in Pacific Yew," *Biochem.* 35:2968–2977 (1996).
Mau et al., "Cloning of Casbene Synthase cDNA: Evidence for Conserved Structural Features Among Terpeonid Cyclases in Plants," *Proc. Natl. Acad. Sci. USA* 91:8497–8501 (1994).
McGarvey et al., "Terpenoid Metabolism," *Plant Cell* 7:1015–1026 (1995).
Orth et al., "Characterization of a cDNA Encoding a Manganese Peroxidase from Phanerocheate chrysosporium: Genomic Organization of Lignin and Manganese Peroxidase–Encoding Genes," Gene:161–165 (1994).
Rajaonarivony et al., "Evidence for an Essential Histadine Residue in 4S–Limonene Synthase and Other Terpene Cyclases," *Arch Biochem. Biophy.* 299:77–82 (1992).
Rubenstein et al., "Studies on the Biosynthesis of Taxol: Total Synthesis of Taxa–4(20),11(12)–diene and Taxa–4(5), 11(12)–diene. The First Committed Biosynthetic Intermediate," *J. Org. Chem.* 60:7215–7223 (1995).
Savage, "Monoterpene Synthases from Gymnosperms and Angiosperms: Stereospecificity and Inactivation by Cysteinyl– and Arginyl–Directed Modifying Reagents," *Arch. Biochem. Biophy.* 320:257–265 (1995).
Scolnik et al., "A Table of Some Cloned Plant Genes Involved in Isoprenoid Biosynthesis," *Plant Mol. Biol. Rep.*, 14:305–319 (1996).
Sun et al., "The Arabidopsis GA1 Locus Encodes the Cyclase ent–Kaurene Synthetase A of Gibberellin Biosynthesis," *The Plant Cell* 6:1509–1518 (1994).
Tarshis et al., "Crystal Structure of Recombinant Farnesyl Diphosphate Synthase at 2.6–Å Resolution," *Biochem.* 33:10871–10877 (1994).
Vogel et al., "Abietadiene Synthase from Grand Fir (*Abies grandis*)," *J. Biol. Chem.* 271:23262–23268 (1996).
West et al., "Regulation of Terpenoid Biosynthesis in Higher Plants," *Rec. Adv. Phytochem.* 13:163–198 (1979).
West, In Biosynthesis of Isoprenoid Compounds, Porter et al. (eds.), vol. 1, pp. 375–411, Wiley & Sons, New York, NY (1981).
Wildung et al., "A cDNA Clone for Taxadiene Synthase, the Diterpene Cyclase that Catalyzes the Committed Step of Taxol Biosynthesis," *J. Biol. Chem.* 271:9201–9204 (1996).

*Primary Examiner*—Ponnathapu Achutamurthy
*Assistant Examiner*—Tekchand Saidha
*Attorney, Agent, or Firm*—Klarquist Sparkman Campbell Leigh & Whinston, LLP

[57] ABSTRACT

The taxadiene synthase gene of Pacific yew has been cloned and its nucleic acid and polypeptide sequence is presented. Truncation or removal of the transit peptide increases expression of the cloned taxadiene synthase gene expression in *E. coli* cells.

9 Claims, 3 Drawing Sheets

Geranylgeranyl diphosphate → Taxa-4(5),11(12)-diene → → → Taxol

```
   1 TTCCCCTGCCTCTCTGAGAAATGGCTCAGCTCTCATTAATGCAGCGCTGAAGATGAACGCATTGGGAACAAGGCAATCCACGATCCA         90
   1                   M  A  Q  L  S  F  N  A  A  L  K  M  N  A  L  G  N  K  A  I  H  D  P         23
  91 ACGAATTGCAGAGCCAAATCTGAGCGCCAAATGATGTGGGTTTGCTCCAGATCAGGGCGAACCAGAGTAAAATGTCGAGAGAAGTGGT        180
  24  T  N  C  R  A  K  S  E  R  Q  M  M  W  V  C  S  R  S  G  R  T  R  V  K  M  S  R  G  S  G      53
 181 GGTCCTGGTCCTGTCGTAATGATGAGCAGCAGCACTGGCACTAGCAAGGTGGTTTCCGAGACTTCCAGTACCATTGTGGATGATATCCCT        270
  54  G  P  G  P  V  V  M  M  S  S  S  T  G  T  S  K  V  V  S  E  T  S  S  T  I  V  D  D  I  P      83
 271 CGACTCTCCGCCAATTATCATGGCGATCTGTGGCACCACAATGTTATACAAACTCTGGAGACACCGTTTCGTGAGAGTTCTACTTACCAA       360
  84  R  L  S  A  N  Y  H  G  D  L  W  H  H  N  V  I  Q  T  L  E  T  P  F  R  E  S  S  T  Y  Q     113
 361 GAACGGGCAGATGAGCTGGTTGTGAAATTAAAGATATGTTCAATGCGCTCGGAGACGGAGATATCAGTCCGTCTGCATACGACACTGCG       450
 114  E  R  A  D  E  L  V  V  K  I  K  D  M  F  N  A  L  G  D  G  D  I  S  P  S  A  Y  D  T  A     143
 451 TGGGTGGCGAGGCTGGCGACCATTTCCTCTGATGGATCTGAGAAGCCACGGTTTCCTCAGGCCCTCAACTGGTTTCAACAACCAGCTC       540
 144  W  V  A  R  L  A  T  I  S  S  D  G  S  E  K  P  R  F  P  Q  A  L  N  W  F  N  N  Q  L     173
 541 CAGGATGGATCGTGGGGATCGAATCGCCACTTTAGTTTATGCGATCGATTGCTTAACGACGAATCTGTGTTATCGCCTCTCGGTTTGG       630
 174  Q  D  G  S  W  G  I  E  S  H  F  S  L  C  D  R  L  L  N  T  T  N  S  V  I  A  L  S  V  W     203
 631 AAAACAGGGCACAGCCAAGTACAACAAGGTGCTGAGTTTATTGCAGAGAATCTAAGATTACTCAATGAGGAAGATGAGTTGTCCCCGGAT       720
 204  K  T  G  H  S  Q  V  Q  Q  G  A  E  F  I  A  E  N  L  R  L  L  N  E  E  D  E  L  S  P  D     233
 721 TTCCAAATAATCTTTCCTGCTCTGCTCCAAAAGGCAAAAGCGTTGGGGATCAATATTCCAGCCAACATGTTGAATGCGTTGGAAGGCTCTCGAGGAA  810
 234  F  Q  I  I  F  P  A  L  L  Q  K  A  K  A  L  G  I  N  I  P  A  N  M  L  N  A  L  E  G  L  E  E  263
 811 ACAACACGGGAAGCCAGGCTTACAGATGTTTCTGCGGCAGCAGCTGACAATATTCCAGCCAACATGTTCCTGAGCTCCCCTGCTTCCACTGCTGTGTACTGTGATGAATT  900
 264  T  T  R  E  A  R  L  T  D  V  S  A  A  A  D  N  I  P  A  N  M  L  E  G  L  E  E     293
 901 GTTATTGACTGGAACAAGATTATGAGGTTTCAAAGTAAAGATGGATCTTTCAAGGATGGGTCGTTCCTGAGCTCCCCTGCTTCCACTGCTGTGTACTGTGATGAATT     990
 294  V  I  D  W  N  K  I  M  R  F  Q  S  K  D  G  S  F  L  S  S  P  A  S  T  A  C  V  L  M  N     323
 991 ACAGGGACGAAAAAATGTTCACTTTTCCAACAATTGAGCATTCCGAACATCGGTCGCTCGACATCTGCTCAAATCAAAGGAGCTCTTGATTATGTCTAC      1080
 324  T  G  D  E  K  C  F  T  F  L  N  N  L  L  D  K  F  G  G  C  V  P  C  M  Y  S  I  D  L  L     353
1081 GAACGCCTTTCGCTGGTTGATAACATTGAGCATCTCGGAATCGGTCGCCATTCAACCAGTCAACACCACAGCCCTGTTCTTCAAGATCTCAACAGCTCAACACCACAGCCCTGGT  1170
 354  E  R  L  S  L  V  D  N  I  E  H  L  G  I  G  R  H  F  K  Q  E  I  K  G  A  L  D  Y  V  Y     383
1171 AGACATTGGAGTGAAAGGGGCATCGGTTGGGATGGGGAGACAGCCCTTGTTCCAGATCTCAACACCGCGCTGGGCGCCCTGCGAACTCTTCGC  1260
 384  R  H  W  S  E  R  G  I  G  W  G  R  D  S  L  V  P  D  L  N  T  T  A  L  G  L  R  T  L  R     413
1261 ATGCACGGATACAATGTTTCTTCAGACGTTTTGAATAATTTCAAAGATGAAAACGGGCGTTTCTTCTCTGCGGCCAAACCCATGTC       1350
 414  M  H  G  Y  N  V  S  S  D  V  L  N  N  F  K  D  E  N  G  R  F  F  S  A  G  Q  T  H  V     443
```

FIG. 2A

```
1351  GAATTGAGAAGCGTGGTGAATCTTTTCAGAGCTTCCGACCTTGCATTTCCTGACGAAAGAGCTATGGACGATGCTAGAAAATTTGCAGAA   1440
 444   E  L  R  S  V  V  N  L  F  R  A  S  D  L  A  F  P  D  E  R  A  M  D  D  A  R  K  F  A  E    473
1441  CCATATCTTAGAGAGGCACTTGCAACGAATCTCAACGAAATATTCAAAGAGATTGAGTACGTGGTGGAGTACCCTTGGCAC           1530
 474   P  Y  L  R  E  A  L  A  T  K  I  S  T  N  T  K  L  F  K  E  I  E  Y  V  V  E  Y  P  W  H    503
1531  ATGAGTATCCCACGCTTAGAAGCCAGAAGTTATATATTGATTCATATGACGACAATTATGATGGCAGAGGAAGACTCTATATAGAATGCCA  1620
 504   M  S  I  P  R  L  E  A  R  S  Y  I  D  S  Y  D  D  N  Y  V  W  Q  R  K  T  L  Y  R  M  P    533
1621  TCTTTGAGTAATTCAAAATGTTTAGAAATTGGCAAAATTGGACTTCAATATCGTACAATCTTTGCATCAAGAGGAGTTGAAGCTTCTAACA  1710
 534   S  L  S  N  S  K  C  L  E  L  A  K  L  D  F  N  I  V  Q  S  L  H  Q  E  E  L  K  L  L  T    563
1711  AGATGGTGGAAGGAATCCGGCATGGCAGATATAAATTTCACTCGACACCGAGTGGCGGAGGTTTATTTTTCATCAGCTACATTTGAACCC   1800
 564   R  W  W  K  E  S  G  M  A  D  I  N  F  T  R  H  R  V  A  E  V  Y  F  S  S  A  T  F  E  P    593
1801  GAATATTCTGCCACTAGAATTGCCTTCACAAAAATTGGTGTTGTTCAAGTCTTTTGATGATATGGCTGACATCTTTGCAACACTAGAT    1890
 594   E  Y  S  A  T  R  I  A  F  T  K  I  G  C  L  Q  V  L  F  D  D  M  A  D  I  F  A  T  L  D    623
1891  GAATTGAAAAGTTTCACTGAGGGAGTAAAGAGAGTGGGATACATCTTTGCTACATGAGATTCCAGAGTGTATGCAAACTTGCTTTAAAGTT  1980
 624   E  L  K  S  F  T  E  G  V  K  R  W  D  T  S  L  L  H  E  I  P  E  C  M  Q  T  C  F  K  V    653
1981  TGGTTCAAATTAATGGAAGAAGTAATAATGATGTGGTTAAGTACAAGGACCGGGTATATACCAACTTTTGAAGAGTACTTAAAGACTTATGCTATATCA  2070
 654   W  F  K  L  M  E  E  V  N  N  D  V  V  K  V  Q  G  R  D  M  L  A  H  I  R  K  P  W  E  L    683
2071  TACTTCAATTGTTATGTACAAGAAAGGGAGTGGCTTGAAGCTGGGTGAGCTTGTTGAAGATGATGTTGAAAAGTGCACTATCCCTCA     2160
 684   Y  F  N  C  Y  V  Q  E  R  E  W  L  E  A  G  Y  I  P  T  F  E  E  Y  L  K  T  Y  A  I  S    713
2161  GTAGGCCTTGGACCGTGTACCTGTGTATCCTTGAGCTTGTTGTGAAGATGATGTTGAGCTTGTTGAAGATGATGTTGAGAAAGTGCACTATCCCTCA  2250
 714   V  G  L  G  P  C  T  L  Q  P  I  L  L  M  G  E  L  V  K  D  D  V  E  K  V  H  Y  P  S    743
2251  AATATGTTTGAGCTTGTATCCTTGAGCTGGCGACTAATCCAGGAGCAACTAATATCCCTGAGGAGAATGCACACAAAACATATCAGGCTGAAAAGGCTCGAGGACAACAAGCCTCA  2340
 744   N  M  F  E  L  V  S  L  S  W  R  L  T  N  D  T  K  T  Y  Q  A  E  K  A  R  G  Q  Q  A  S    773
2341  GGCATAGCATGCTATATGAAGGATAATCCAGGAGCAACTGAGGAAGATGCCATTAAGCACATATGTCGTGTTGATCGGGCCTTGAAA    2430
 774   G  I  A  C  Y  M  K  D  N  P  G  A  T  E  E  D  A  I  K  H  I  C  R  V  V  D  R  A  L  K    803
2431  GAAGCAAGCTTTGAATATTTCAAACATCCAATGGGTTGCAAGTCTTCCTTTATTTTTAACCTTAGATTGTGTGTCCAAATC          2520
 804   E  A  S  F  E  Y  F  K  P  S  N  D  I  P  M  G  C  K  S  F  I  F  N  L  R  L  C  V  Q  I    833
2521  TTTTACAAGTTTATAGATGGGTACGGAATCGCCAATGAGAGATTAAGGACTATATAAGAAAAGTTTATATTGATCCAATTCAAGTATGA    2610
 834   F  Y  K  F  I  D  G  Y  G  I  A  N  E  E  I  K  D  Y  I  R  K  V  Y  I  D  P  I  Q  V  *    862
2611  TATATCATGTAAAACCCTCTTTTTCATGATAAATTGACTTATTATTGTATTGGCAAAAAAAAAAAAAAAAAAA                   2700
```

FIG. 2B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2700 base pairs
      (B) TYPE: nucleic acid
      (C) STRANDEDNESS: double stranded
      (D) TOPOLOGY: linear (xi) SEQUENCE DESCRIPTION: SEQ ID NO:1:

```
TTCCCCTGCC TCTCTGGAGA A                                          21

ATG GCT CAG CTC TCA TTT AAT GCA GCG CTG AAG ATG AAC GCA TTG GGG    69
Met Ala Gln Leu Ser Phe Asn Ala Ala Leu Lys Met Asn Ala Leu Gly
              5                  10                  15

AAC AAG GCA ATC CAC GAT CCA ACG AAT TGC AGA GCC AAA TCT GAG CGC   117
Asn Lys Ala Ile His Asp Pro Thr Asn Cys Arg Ala Lys Ser Glu Arg
             20                  25                  30

CAA ATG ATG TGG GTT TGC TCC AGA TCA GGG CGA ACC AGA GTA AAA ATG   165
Gln Met Met Trp Val Cys Ser Arg Ser Gly Arg Thr Arg Val Lys Met
         35                  40                  45

TCG AGA GGA AGT GGT GGT CCT GGT CCT GTC GTA ATG ATG AGC AGC AGC   213
Ser Arg Gly Ser Gly Gly Pro Gly Pro Val Val Met Met Ser Ser Ser
     50                  55                  60

ACT GGC ACT AGC AAG GTG GTT TCC GAG ACT TCC AGT ACC ATT GTG GAT   261
Thr Gly Thr Ser Lys Val Val Ser Glu Thr Ser Ser Thr Ile Val Asp
 65                  70                  75                  80
```

-continued

```
GAT ATC CCT CGA CTC TCC GCC AAT TAT CAT GGC GAT CTG TGG CAC CAC       309
Asp Ile Pro Arg Leu Ser Ala Asn Tyr His Gly Asp Leu Trp His His
                85                  90                  95

AAT GTT ATA CAA ACT CTG GAG ACA CCG TTT CGT GAG AGT TCT ACT TAC       357
Asn Val Ile Gln Thr Leu Glu Thr Pro Phe Arg Glu Ser Ser Thr Tyr
            100                 105                 110

CAA GAA CGG GCA GAT GAG CTG GTT GTG AAA ATT AAA GAT ATG TTC AAT       405
Gln Glu Arg Ala Asp Glu Leu Val Val Lys Ile Lys Asp Met Phe Asn
            115                 120                 125

GCG CTC GGA GAC GGA GAT ATC AGT CCG TCT GCA TAC GAC ACT GCG TGG       453
Ala Leu Gly Asp Gly Asp Ile Ser Pro Ser Ala Tyr Asp Thr Ala Trp
        130                 135                 140

GTG GCG AGG CTG GCG ACC ATT TCC TCT GAT GGA TCT GAG AAG CCA CGG       501
Val Ala Arg Leu Ala Thr Ile Ser Ser Asp Gly Ser Glu Lys Pro Arg
145                 150                 155                 160

TTT CCT CAG GCC CTC AAC TGG GTT TTC AAC AAC CAG CTC CAG GAT GGA       549
Phe Pro Gln Ala Leu Asn Trp Val Phe Asn Asn Gln Leu Gln Asp Gly
                165                 170                 175

TCG TGG GGT ATC GAA TCG CAC TTT AGT TTA TGC GAT CGA TTG CTT AAC       597
Ser Trp Gly Ile Glu Ser His Phe Ser Leu Cys Asp Arg Leu Leu Asn
                180                 185                 190

ACG ACC AAT TCT GTT ATC GCC CTC TCG GTT TGG AAA ACA GGG CAC AGC       645
Thr Thr Asn Ser Val Ile Ala Leu Ser Val Trp Lys Thr Gly His Ser
            195                 200                 205

CAA GTA CAA CAA GGT GCT GAG TTT ATT GCA GAG AAT CTA AGA TTA CTC       693
Gln Val Gln Gln Gly Ala Glu Phe Ile Ala Glu Asn Leu Arg Leu Leu
        210                 215                 220

AAT GAG GAA GAT GAG TTG TCC CCG GAT TTC CAA ATA ATC TTT CCT GCT       741
Asn Glu Glu Asp Glu Leu Ser Pro Asp Phe Gln Ile Ile Phe Pro Ala
225                 230                 235                 240

CTG CTG CAA AAG GCA AAA GCG TTG GGG ATC AAT CTT CCT TAC GAT CTT       789
Leu Leu Gln Lys Ala Lys Ala Leu Gly Ile Asn Leu Pro Tyr Asp Leu
                245                 250                 255

CCA TTT ATC AAA TAT TTG TCG ACA ACA CGG GAA GCC AGG CTT ACA GAT       837
Pro Phe Ile Lys Tyr Leu Ser Thr Thr Arg Glu Ala Arg Leu Thr Asp
                260                 265                 270

GTT TCT GCG GCA GCA GAC AAT ATT CCA GCC AAC ATG TTG AAT GCG TTG       885
Val Ser Ala Ala Ala Asp Asn Ile Pro Ala Asn Met Leu Asn Ala Leu
            275                 280                 285

GAA GGT CTC GAG GAA GTT ATT GAC TGG AAC AAG ATT ATG AGG TTT CAA       933
Glu Gly Leu Glu Glu Val Ile Asp Trp Asn Lys Ile Met Arg Phe Gln
        290                 295                 300

AGT AAA GAT GGA TCT TTC CTG AGC TCC CCT GCC TCC ACT GCC TGT GTA       981
Ser Lys Asp Gly Ser Phe Leu Ser Ser Pro Ala Ser Thr Ala Cys Val
305                 310                 315                 320

CTG ATG AAT ACA GGG GAC GAA AAA TGT TTC ACT TTT CTC AAC AAT CTG      1029
Leu Met Asn Thr Gly Asp Glu Lys Cys Phe Thr Phe Leu Asn Asn Leu
                325                 330                 335

CTC GAC AAA TTC GGC GGC TGC GTG CCC TGT ATG TAT TCC ATC GAT CTG      1077
Leu Asp Lys Phe Gly Gly Cys Val Pro Cys Met Tyr Ser Ile Asp Leu
                340                 345                 350

CTG GAA CGC CTT TCG CTG GTT GAT AAC ATT GAG CAT CTC GGA ATC GGT      1125
Leu Glu Arg Leu Ser Leu Val Asp Asn Ile Glu His Leu Gly Ile Gly
            355                 360                 365

CGC CAT TTC AAA CAA GAA ATC AAA GGA GCT CTT GAT TAT GTC TAC AGA      1173
Arg His Phe Lys Gln Glu Ile Lys Gly Ala Leu Asp Tyr Val Tyr Arg
        370                 375                 380

CAT TGG AGT GAA AGG GGC ATC GGT TGG GGC AGA GAC AGC CTT GTT CCA      1221
His Trp Ser Glu Arg Gly Ile Gly Trp Gly Arg Asp Ser Leu Val Pro
```

-continued

```
385                 390                 395                 400

GAT CTC AAC ACC ACA GCC CTC GGC CTG CGA ACT CTT CGC ATG CAC GGA        1269
Asp Leu Asn Thr Thr Ala Leu Gly Leu Arg Thr Leu Arg Met His Gly
                    405                 410                 415

TAC AAT GTT TCT TCA GAC GTT TTG AAT AAT TTC AAA GAT GAA AAC GGG        1317
Tyr Asn Val Ser Ser Asp Val Leu Asn Asn Phe Lys Asp Glu Asn Gly
                420                 425                 430

CGG TTC TTC TCC TCT GCG GGC CAA ACC CAT GTC GAA TTG AGA AGC GTG        1365
Arg Phe Phe Ser Ser Ala Gly Gln Thr His Val Glu Leu Arg Ser Val
            435                 440                 445

GTG AAT CTT TTC AGA GCT TCC GAC CTT GCA TTT CCT GAC GAA AGA GCT        1413
Val Asn Leu Phe Arg Ala Ser Asp Leu Ala Phe Pro Asp Glu Arg Ala
        450                 455                 460

ATG GAC GAT GCT AGA AAA TTT GCA GAA CCA TAT CTT AGA GAG GCA CTT        1461
Met Asp Asp Ala Arg Lys Phe Ala Glu Pro Tyr Leu Arg Glu Ala Leu
465                 470                 475                 480

GCA ACG AAA ATC TCA ACC AAT ACA AAA CTA TTC AAA GAG ATT GAG TAC        1509
Ala Thr Lys Ile Ser Thr Asn Thr Lys Leu Phe Lys Glu Ile Glu Tyr
                    485                 490                 495

GTG GTG GAG TAC CCT TGG CAC ATG AGT ATC CCA CGC TTA GAA GCC AGA        1557
Val Val Glu Tyr Pro Trp His Met Ser Ile Pro Arg Leu Glu Ala Arg
                500                 505                 510

AGT TAT ATT GAT TCA TAT GAC GAC AAT TAT GTA TGG CAG AGG AAG ACT        1605
Ser Tyr Ile Asp Ser Tyr Asp Asp Asn Tyr Val Trp Gln Arg Lys Thr
            515                 520                 525

CTA TAT AGA ATG CCA TCT TTG AGT AAT TCA AAA TGT TTA GAA TTG GCA        1653
Leu Tyr Arg Met Pro Ser Leu Ser Asn Ser Lys Cys Leu Glu Leu Ala
        530                 535                 540

AAA TTG GAC TTC AAT ATC GTA CAA TCT TTG CAT CAA GAG GAG TTG AAG        1701
Lys Leu Asp Phe Asn Ile Val Gln Ser Leu His Gln Glu Glu Leu Lys
545                 550                 555                 560

CTT CTA ACA AGA TGG TGG AAG GAA TCC GGC ATG GCA GAT ATA AAT TTC        1749
Leu Leu Thr Arg Trp Trp Lys Glu Ser Gly Met Ala Asp Ile Asn Phe
                    565                 570                 575

ACT CGA CAC CGA GTG GCG GAG GTT TAT TTT TCA TCA GCT ACA TTT GAA        1797
Thr Arg His Arg Val Ala Glu Val Tyr Phe Ser Ser Ala Thr Phe Glu
                580                 585                 590

CCC GAA TAT TCT GCC ACT AGA ATT GCC TTC ACA AAA ATT GGT TGT TTA        1845
Pro Glu Tyr Ser Ala Thr Arg Ile Ala Phe Thr Lys Ile Gly Cys Leu
            595                 600                 605

CAA GTC CTT TTT GAT GAT ATG GCT GAC ATC TTT GCA ACA CTA GAT GAA        1893
Gln Val Leu Phe Asp Asp Met Ala Asp Ile Phe Ala Thr Leu Asp Glu
        610                 615                 620

TTG AAA AGT TTC ACT GAG GGA GTA AAG AGA TGG GAT ACA TCT TTG CTA        1941
Leu Lys Ser Phe Thr Glu Gly Val Lys Arg Trp Asp Thr Ser Leu Leu
625                 630                 635                 640

CAT GAG ATT CCA GAG TGT ATG CAA ACT TGC TTT AAA GTT TGG TTC AAA        1989
His Glu Ile Pro Glu Cys Met Gln Thr Cys Phe Lys Val Trp Phe Lys
                    645                 650                 655

TTA ATG GAA GAA GTA AAT AAT GAT GTG GTT AAG GTA CAA GGA CGT GAC        2037
Leu Met Glu Glu Val Asn Asn Asp Val Val Lys Val Gln Gly Arg Asp
                660                 665                 670

ATG CTC GCT CAC ATA AGA AAA CCC TGG GAG TTG TAC TTC AAT TGT TAT        2085
Met Leu Ala His Ile Arg Lys Pro Trp Glu Leu Tyr Phe Asn Cys Tyr
            675                 680                 685

GTA CAA GAA AGG GAG TGG CTT GAA GCC GGG TAT ATA CCA ACT TTT GAA        2133
Val Gln Glu Arg Glu Trp Leu Glu Ala Gly Tyr Ile Pro Thr Phe Glu
        690                 695                 700

GAG TAC TTA AAG ACT TAT GCT ATA TCA GTA GGC CTT GGA CCG TGT ACC        2181
```

```
Glu Tyr Leu Lys Thr Tyr Ala Ile Ser Val Gly Leu Gly Pro Cys Thr
705                 710                 715                 720

CTA CAA CCA ATA CTA CTA ATG GGT GAG CTT GTG AAA GAT GAT GTT GTT    2229
Leu Gln Pro Ile Leu Leu Met Gly Glu Leu Val Lys Asp Asp Val Val
                725                 730                 735

GAG AAA GTG CAC TAT CCC TCA AAT ATG TTT GAG CTT GTA TCC TTG AGC    2277
Glu Lys Val His Tyr Pro Ser Asn Met Phe Glu Leu Val Ser Leu Ser
            740                 745                 750

TGG CGA CTA ACA AAC GAC ACC AAA ACA TAT CAG GCT GAA AAG GCT CGA    2325
Trp Arg Leu Thr Asn Asp Thr Lys Thr Tyr Gln Ala Glu Lys Ala Arg
        755                 760                 765

GGA CAA CAA GCC TCA GGC ATA GCA TGC TAT ATG AAG GAT AAT CCA GGA    2373
Gly Gln Gln Ala Ser Gly Ile Ala Cys Tyr Met Lys Asp Asn Pro Gly
    770                 775                 780

GCA ACT GAG GAA GAT GCC ATT AAG CAC ATA TGT CGT GTT GTT GAT CGG    2421
Ala Thr Glu Glu Asp Ala Ile Lys His Ile Cys Arg Val Val Asp Arg
785                 790                 795                 800

GCC TTG AAA GAA GCA AGC TTT GAA TAT TTC AAA CCA TCC AAT GAT ATC    2469
Ala Leu Lys Glu Ala Ser Phe Glu Tyr Phe Lys Pro Ser Asn Asp Ile
                805                 810                 815

CCA ATG GGT TGC AAG TCC TTT ATT TTT AAC CTT AGA TTG TGT GTC CAA    2517
Pro Met Gly Cys Lys Ser Phe Ile Phe Asn Leu Arg Leu Cys Val Gln
            820                 825                 830

ATC TTT TAC AAG TTT ATA GAT GGG TAC GGA ATC GCC AAT GAG GAG ATT    2565
Ile Phe Tyr Lys Phe Ile Asp Gly Tyr Gly Ile Ala Asn Glu Glu Ile
        835                 840                 845

AAG GAC TAT ATA AGA AAA GTT TAT ATT GAT CCA ATT CAA GTA TGA        2610
Lys Asp Tyr Ile Arg Lys Val Tyr Ile Asp Pro Ile Gln Val
    850                 855                 860

TATATCATGT AAAACCTCTT TTTCATGATA AATTGACTTA TTATTGTATT GGCAAAAAAA  2670

AAAAAAAAAA AAAAAAAAAA AAAAAAAAAA                                    2700

(2) INFORMATION FOR SEQ ID NO: 2:

(i) SEQUENCE CHARACTERISTICS:
        (A) LENGTH: 862 amino acid residues
        (B) TYPE:   amino acid
        (C) STRANDEDNESS: single stranded
        (D) TOPOLOGY: linear (xi) SEQUENCE DESCRIPTION: SEQ ID NO:2:

Met Ala Gln Leu Ser Phe Asn Ala Ala Leu Lys Met Asn Ala Leu Gly
                5                  10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Pro Gly Pro Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
```

```
                130                 135                 140
Val Ala Arg Leu Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
                180                 185                 190

Thr Thr Asn Ser Val Ile Ala Leu Ser Val Trp Lys Thr Gly His Ser
                195                 200                 205

Gln Val Gln Gln Gly Ala Glu Phe Ile Ala Glu Asn Leu Arg Leu Leu
                210                 215                 220

Asn Glu Glu Asp Glu Leu Ser Pro Asp Phe Gln Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
                260                 265                 270

Val Ser Ala Ala Ala Asp Asn Ile Pro Ala Asn Met Leu Asn Ala Leu
                275                 280                 285

Glu Gly Leu Glu Glu Val Ile Asp Trp Asn Lys Ile Met Arg Phe Gln
                290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
                355                 360                 365

Arg His Phe Lys Gln Glu Ile Lys Gly Ala Leu Asp Tyr Val Tyr Arg
                370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Met His Gly
                405                 410                 415

Tyr Asn Val Ser Ser Asp Val Leu Asn Asn Phe Lys Asp Glu Asn Gly
                420                 425                 430

Arg Phe Phe Ser Ser Ala Gly Gln Thr His Val Glu Leu Arg Ser Val
                435                 440                 445

Val Asn Leu Phe Arg Ala Ser Asp Leu Ala Phe Pro Asp Glu Arg Ala
                450                 455                 460

Met Asp Asp Ala Arg Lys Phe Ala Glu Pro Tyr Leu Arg Glu Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Arg
                500                 505                 510

Ser Tyr Ile Asp Ser Tyr Asp Asp Asn Tyr Val Trp Gln Arg Lys Thr
                515                 520                 525

Leu Tyr Arg Met Pro Ser Leu Ser Asn Ser Lys Cys Leu Glu Leu Ala
                530                 535                 540

Lys Leu Asp Phe Asn Ile Val Gln Ser Leu His Gln Glu Glu Leu Lys
545                 550                 555                 560
```

```
Leu Leu Thr Arg Trp Trp Lys Glu Ser Gly Met Ala Asp Ile Asn Phe
            565                 570                 575
Thr Arg His Arg Val Ala Glu Val Tyr Phe Ser Ser Ala Thr Phe Glu
            580                 585                 590
Pro Glu Tyr Ser Ala Thr Arg Ile Ala Phe Thr Lys Ile Gly Cys Leu
            595                 600                 605
Gln Val Leu Phe Asp Asp Met Ala Asp Ile Phe Ala Thr Leu Asp Glu
            610                 615                 620
Leu Lys Ser Phe Thr Glu Gly Val Lys Arg Trp Asp Thr Ser Leu Leu
625                 630                 635                 640
His Glu Ile Pro Glu Cys Met Gln Thr Cys Phe Lys Val Trp Phe Lys
            645                 650                 655
Leu Met Glu Glu Val Asn Asn Asp Val Val Lys Val Gln Gly Arg Asp
            660                 665                 670
Met Leu Ala His Ile Arg Lys Pro Trp Glu Leu Tyr Phe Asn Cys Tyr
            675                 680                 685
Val Gln Glu Arg Glu Trp Leu Glu Ala Gly Tyr Ile Pro Thr Phe Glu
            690                 695                 700
Glu Tyr Leu Lys Thr Tyr Ala Ile Ser Val Gly Leu Gly Pro Cys Thr
705                 710                 715                 720
Leu Gln Pro Ile Leu Leu Met Gly Glu Leu Val Lys Asp Asp Val Val
            725                 730                 735
Glu Lys Val His Tyr Pro Ser Asn Met Phe Glu Leu Val Ser Leu Ser
            740                 745                 750
Trp Arg Leu Thr Asn Asp Thr Lys Thr Tyr Gln Ala Glu Lys Ala Arg
            755                 760                 765
Gly Gln Gln Ala Ser Gly Ile Ala Cys Tyr Met Lys Asp Asn Pro Gly
            770                 775                 780
Ala Thr Glu Glu Asp Ala Ile Lys His Ile Cys Arg Val Val Asp Arg
785                 790                 795                 800
Ala Leu Lys Glu Ala Ser Phe Gly Tyr Phe Lys Pro Ser Asn Asp Ile
            805                 810                 815
Pro Met Gly Cys Lys Ser Phe Ile Phe Asn Leu Arg Leu Cys Val Gln
            820                 825                 830
Ile Phe Tyr Lys Phe Ile Asp Gly Tyr Gly Ile Ala Asn Glu Glu Ile
            835                 840                 845
Lys Asp Tyr Ile Arg Lys Val Tyr Ile Asp Pro Ile Gln Val
850                 855                 860
```

(2) INFORMATION FOR SEQ ID NO: 3:

(i) SEQUENCE CHARACTERISTICS:
        (A) LENGTH: 5 amino acid residues
        (B) TYPE: amino acid
        (C) STRANDEDNESS: single stranded
        (D) TOPOLOGY: linear (xi) SEQUENCE DESCRIPTION: SEQ ID NO:3:
```
Asp Asp Xaa Xaa Asp
            5
```

(2) INFORMATION FOR SEQ ID NO: 4:

(i) SEQUENCE CHARACTERISTICS:
        (A) LENGTH: 5 amino acid residues
        (B) TYPE: amino acid
        (C) STRANDEDNESS: single stranded
        (D) TOPOLOGY: linear

```
    (xi) SEQUENCE DESCRIPTION:  SEQ ID NO:4:
Asp Xaa Xaa Asp Asp
              5

(2) INFORMATION FOR SEQ ID NO: 5:

(i) SEQUENCE CHARACTERISTICS:
        (A) LENGTH: 4 amino acid residues
        (B) TYPE:   amino acid
        (C) STRANDEDNESS:  single stranded
        (D) TOPOLOGY:  linear (xi) SEQUENCE DESCRIPTION:  SEQ ID NO:5:

Arg Trp Trp Lys (2) INFORMATION FOR SEQ ID NO: 6:

(i) SEQUENCE CHARACTERISTICS:
        (A) LENGTH: 9 amino acid residues
        (B) TYPE:   amino acid
        (C) STRANDEDNESS:  single stranded
        (D) TOPOLOGY:  linear (xi) SEQUENCE DESCRIPTION:  SEQ ID NO:6:

Xaa Xaa Asp Asp Xaa Xaa Xaa Xaa Asp
```

COMPOSITIONS AND METHODS FOR TAXOL BIOSYNTHESIS

CROSS REFERENCE TO RELATED CASE

This application is a divisional of U.S. application Ser. No. 08/843,363 now U.S. Pat. No. 5,994,114, and claims the benefit under 35 U.S.C. § 120 to U.S. Provisional Application No. 60/015,993, filed Apr. 15, 1996, incorporated herein by reference.

ACKNOWLEDGMENT OF GOVERNMENT SUPPORT

This invention was made with government support under National Institutes of Health Grant No. CA-55254. The government has certain rights in this invention.

TECHNICAL FIELD

This invention is related to the field of detection of diterpenoid biosynthesis, particularly to the biosynthesis of taxoid compounds such as Taxol.

BACKGROUND ART

The highly functionalized diterpenoid Taxol (Wani et al., *J. Am. Chem. Soc.* 93:2325–2327, 1971) is well-established as a potent chemotherapeutic agent (Holmes et al., in *Taxane Anticancer Agents: Basic Science and Current Status*, Georg et al., eds., pp. 31–57, American Chemical Society, Washington, D.C., 1995; Arbuck and Blaylock, in *Taxol: Science and Applications*, Suffness, ed., pp. 379–415, CRC Press, Boca Raton, Fla., 1995). (Paclitaxel is the generic name for Taxol, a registered trademark of Bristol-Myers Squibb.)

The supply of Taxol from the original source, the bark of the Pacific yew (*Taxus brevifolia* Nutt.; Taxaceae) is limited. As a result, there have been intensive efforts to develop alternate means of production, including isolation from the foliage and other renewable tissues of plantation-grown Taxus species, biosynthesis in tissue culture systems, and semisynthesis of Taxol and its analogs from advanced taxane diterpenoid (taxoid) metabolites that are more readily available (Cragg et al., *J. Nat. Prod.* 56:1657–1668, 1993). Total synthesis of Taxol, at present, is not commercially viable (Borman, *Chem. Eng. News* 72(7):32–34, 1994), and it is clear that in the foreseeable future the supply of Taxol and its synthetically useful progenitors must rely on biological methods of production, either in Taxus plants or in cell cultures derived therefrom (Suffness, in *Taxane Anticancer Agents: Basic Science and Current Status*, Georg et al., eds., American Chemical Society, Washington, D.C., 1995, pp. 1–17).

The biosynthesis of Taxol involves the initial cyclization of geranylgeranyl diphosphate, the universal precursor of diterpenoids (West, in *Biosynthesis of Isoprenoid Compounds*, Porter and Spurgeon, eds., vol. 1, pp. 375–411, Wiley & Sons, New York, N.Y., 1981), to taxa-4(5),11(12)-diene (Koepp et al., *J. Biol. Chem.* 270:8686–8690, 1995) followed by extensive oxidative modification of this olefin (Koepp et al., *J. Biol. Chem.* 270:8686–8690, 1995; Croteau et al., in *Taxane Anticancer Agents: Basic Science and Current Status*, Georg et al., eds., pp. 72–80, American Chemical Society, Washington, D.C., 1995) and elaboration of the side chains (FIG. 1) (Floss and Mocek, in *Taxol: Science and Applications*, Suffness, ed., pp. 191–208, CRC Press, Boca Raton, Fla., 1995).

Taxa-4(5),11(12)-diene synthase ("taxadiene synthase"), the enzyme responsible for the initial cyclization of geranylgeranyl diphosphate, to delineate the taxane skeleton, has been isolated from *T. brevifolia* stem tissue, partially purified, and characterized (Hezari et al., *Arch. Biochem. Biophys.* 322:437–444, 1995).

Although taxadiene synthase resembles other plant terpenoid cyclases in general enzymatic properties (Hezari et al., *Arch. Biochem. Biophys.* 322:437–444, 1995), it has proved extremely difficult to purify in sufficient amounts for antibody preparation or microsequencing, thwarting this approach toward cDNA cloning.

SUMMARY OF THE INVENTION

We have cloned and sequenced the taxadiene synthase gene of Pacific yew.

One embodiment of the invention includes isolated polynucleotides comprising at least 15 consecutive nucleotides, preferably at least 20, more preferably at least 25, and most preferably at least 30 consecutive nucleotides of a native taxadiene synthase gene, e.g., the taxadiene synthase gene of Pacific yew. Such polynucleotides are useful, for example, as probes and primers for obtaining homologs of the taxadiene synthase gene of Pacific yew by, for example, contacting a nucleic acid of a taxoid-producing organism with such a probe or primer under stringent hybridization conditions to permit the probe or primer to hybridize to a taxadiene synthase gene of the organism, then isolating the taxadiene synthase gene of the organism to which the probe or primer hybridizes.

Another embodiment of the invention includes isolated polynucleotides comprising a sequence that encodes a polypeptide having taxadiene synthase biological activity. Preferably, the polypeptide-encoding sequence has at least 70%, preferably at least 80%, and more preferably at least 90% nucleotide sequence similarity with a native Pacific yew taxadiene synthase polynucleotide gene.

In preferred embodiments of such polynucleotides, the polypeptide-encoding sequence encodes a polypeptide having only conservative amino acid substitutions to the native Pacific yew taxadiene synthase polypeptide, except, in some embodiments, for amino acid substitutions at one or more of: cysteine residues 329, 650, 719, and 777; histidine residues 370, 415, 579, and 793; a DDXXD motif (SEQ ID NO: 3); a DXXDD motif (SEQ ID NO: 4); a conserved arginine; and a RWWK element (SEQ ID NO: 5). Preferably, the encoded polypeptide has only conservative amino acid substitutions to or is completely homologous with the native Pacific yew taxadiene synthase polypeptide. In addition, the encoded polypeptide preferably lacks at least part of the transit peptide. Also included are cells, particularly plant cells, and transgenic plants that include such polynucleotides and the encoded polypeptides.

Another embodiment of the invention includes isolated polypeptides having taxadiene synthase activity, preferably having at least 70%, more preferably at least 80%, and most preferably at least 90% homology with a native taxadiene synthase polypeptide. Also included are isolated polypeptides that comprise at least 10, preferably at least 20, more preferably at least 30 consecutive amino acids of a native Pacific yew taxadiene synthase, and most preferably the mature Pacific yew taxadiene synthase polypeptide (i.e., lacking only the transit peptide).

Another embodiment of the invention includes antibodies specific for a native Pacific yew taxadiene synthase polypeptide.

Another embodiment of the invention includes methods of expressing a taxadiene synthase polypeptide in a cell, e.g., a taxoid-producing cell, by culturing a cell that includes an expressible polynucleotide encoding a taxadiene synthase polypeptide under conditions suitable for expression of the polypeptide, preferably resulting in the production of the taxoid at levels that are higher than would be expected from an otherwise similar cell that lacks the expressible polynucleotide.

The foregoing and other objects and advantages of the invention will become more apparent from the following detailed description and accompanying drawings.

BRIEF DESCRIPTION OF THE DRAWINGS

FIG. 2 shows the nucleotide and predicted amino acid sequence of Pacific yew taxadiene synthase clone pTb 42.1 (SEQ ID NO: 1 and SEQ ID NO: 2). The start and stop codons are underlined. The locations of regions employed for primer synthesis are double underlined. The DDMAD and DSYDD motifs (SEQ ID NO: 3 and SEQ ID NO: 4, respectively) are in boldface. Conserved histidines (H) and cysteines (C) and an RWWK element (SEQ ID NO: 7) are indicated by boxes. Truncation sites for removal of part or all of the transit peptide are indicated by a triangle (▼).

DETAILED DESCRIPTION OF THE PREFERRED EMBODIMENTS

Figure 1:
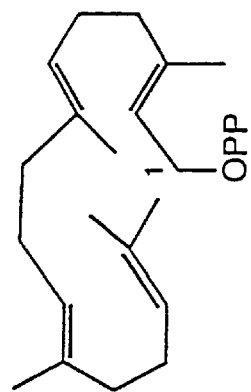
FIG. 1 shows steps in the biosynthesis of Taxol, including the initial cyclization of geranylgeranyl diphosphate to taxa-4(5),11(12)-diene, followed by extensive oxidative modification and elaboration of the side chains.
Figure 1:
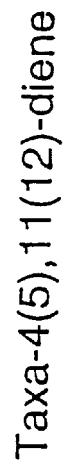
Figure 1:
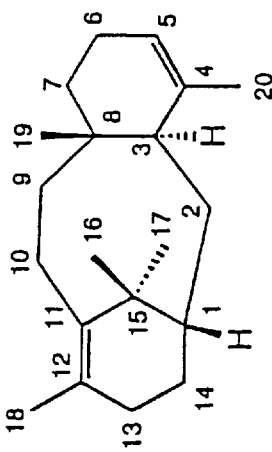
Figure 1:
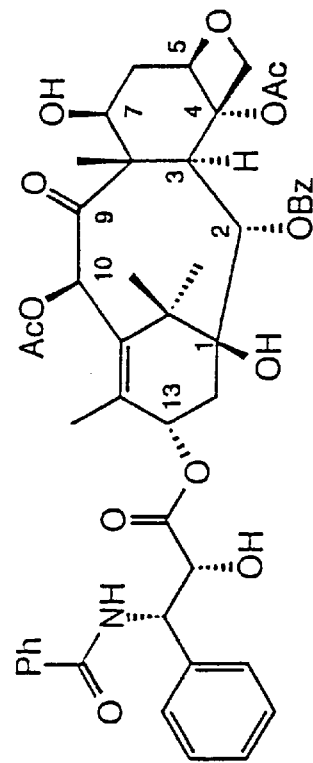

A homology-based cloning strategy using the polymerase chain reaction (PCR) was employed to isolate a cDNA encoding taxadiene synthase. A set of degenerate primers was constructed based on consensus sequences of related monoterpene, sesquiterpene, and diterpene cyclases. Two of these primers amplified a 83 base pair (bp) fragment that was cyclase-like in sequence and that was employed as a hybridization probe to screen a cDNA library constructed from poly(A)$^+$ RNA extracted from Pacific yew stems. Twelve independent clones with insert size in excess of two kilobase pairs (kb) were isolated and partially sequenced.

One of these cDNA isolates was functionally expressed in *Escherichia coli,* yielding a protein that was catalytically active in converting geranylgeranyl diphosphate to a diterpene olefin that was confirmed to be taxa-4(5),11(12)-diene by combined capillary gas chromatography-mass spectrometry (Satterwhite and Croteau, *J. Chromatography* 452:61–73, 1988).

The taxa-4(5),11(12)-diene synthase cDNA sequence specifies an open reading frame of 2586 nucleotides (SEQ ID NO: 1). The deduced polypeptide sequence (SEQ ID NO: 2) contains 862 amino acid residues and has a molecular weight of 98,303, compared to about 79,000 previously determined for the mature native enzyme. It therefore appears to be full-length and includes a long presumptive plastidial targeting peptide. Sequence comparisons with monoterpene, sesquiterpene, and diterpene cyclases of plant origin indicate a significant degree of similarity between these enzymes; the taxadiene synthase most closely resembles (46% identity, 67% similarity) abietadiene synthase, a diterpene cyclase from grand fir.

Uses of the Taxadiene Synthase Gene

Increasing Taxol Biosynthesis in Transformed Cells

The committed step of Taxol (paclitaxel) biosynthesis is the initial cyclization of geranylgeranyl diphosphate, a ubiquitous isoprenoid intermediate, catalyzed by taxadiene synthase, a diterpene cyclase. The product of this reaction is the parent olefin with a taxane skeleton, taxa-4(5),11(12)-diene. For a review of taxoids and taxoid biochemistry, see, e.g., Kingston et al., "The Taxane Diterpenoids," *Progress in the Chemistry of Organic Natural Products,* vol. 61, Springer Verlag, N.Y., 1993, pp. 1–206.

The committed cyclization step of the target pathway is a slow step in the extended biosynthetic sequence leading to Taxol and related taxoids (Koepp et al., *J. Biol. Chem.* 270:8686–8690, 1995; Hezari et al., *Arch. Biochem. Biophys.* 322:437–444, 1995). The yield of Taxol and related taxoids (e.g., cephalomannine, baccatins, taxinines, among others) in cells of an organism capable of taxoid biosynthesis is increased by the expression in such cells of a recombinant taxadiene synthase gene.

This approach to increasing taxoid biosynthesis can be used in any organism that is capable of taxoid biosynthesis. Taxol synthesis is known to take place, for example, in the Taxaceae, including Taxus species from all over the world (including, but not limited to, *T. brevifolia, T. baccata, T. x media, T. cuspidata, T. canadensis,* and *T. chinensis*), as well as in certain microorganisms. Taxol may also be produced by a fungus, *Taxomyces andreanae* (Stierle et al., *Science* 260:214, 1993).

*Agrobacterium tumefaciens*-mediated transformation of Taxus species has been described and the resulting callus cultures shown to produce Taxol (Han et al., *Plant Sci.* 95:187–196, 1994).

Taxol can be isolated from cells transformed with the taxadiene synthase gene by conventional methods. The production of callus and suspension cultures of Taxus, and the isolation of Taxol and related compounds from such cultures, has been described (for example, in Fett-Netto et al., *Bio/Technology* 10: 1572–1575, 1992).

Biosynthesis of Taxoids in Microorganisms

As discussed below, taxadiene synthase activity was observed in transformed *E. coli* host cells expressing recombinant taxadiene synthase. Taxadiene synthase does not require extensive post-translational modification, as provided, for example, in mammalian cells, for enzymatic function. As a result, functional taxadiene synthase can be expressed in a wide variety of host cells.

Geranylgeranyl diphosphate, a substrate of taxadiene synthase, is produced in a wide variety of organisms, including bacteria and yeast that synthesize carotenoid pigments (e.g., Serratia spp. and Rhodotorula spp.). Introduction of vectors capable of expressing taxadiene synthase in such microorganisms permits the production of large amounts of taxa-4(5),11(12)-diene and related compounds having the taxane backbone. The taxane backbone thus produced is useful as a chemical feedstock. Simple taxoids, for example, would be useful as perfume fixatives.

Cloning Taxadiene Synthase Homologs and Related Genes

The availability of the taxadiene synthase gene from Pacific yew makes possible the cloning of homologs of taxadiene synthase from other organisms capable of taxoid biosynthesis, particularly Taxus spp. Although the proportion of common taxoids varies with the species or cultivar of yew tested, apparently all Taxus species synthesize taxoids, including Taxol, to some degree (see, e.g., Mattina and Palva, *J. Environ. Hort.* 10:187–191, 1992; Miller, *J. Natural Products* 43:425–437, 1980). Taxol may also be produced by a fungus, *Taxomyces andreanae* (Stierle et al., *Science* 260:214, 1993).

A taxadiene synthase gene can be isolated from any organism capable of producing Taxol or related taxoids by using primers or probes based on the Pacific yew taxadiene synthase gene sequence or antibodies specific for taxadiene synthase by conventional methods.

Modified Forms of Taxadiene Synthase Gene and Polypeptide

Knowledge of the taxadiene synthase gene sequence permits the modification of the sequence, as described more fully below, to produce variant forms of the gene and the polypeptide gene product. For example, the plastidial transit peptide can be removed and/or replaced by other transit peptides to allow the gene product to be directed to various intracellular compartments or exported from a host cell.

DEFINITIONS AND METHODS

The following definitions and methods are provided to better define the present invention and to guide those of ordinary skill in the art in the practice of the present invention. Definitions of common terms in molecular biology may also be found in Rieger et al., *Glossary of Genetics: Classical and Molecular,* 5th edition, Springer-Verlag, N.Y., 1991; and Lewin, Genes V, Oxford University Press, New York, 1994.

The term "plant" encompasses any plant and progeny thereof. The term also encompasses parts of plants, including seed, cuttings, tubers, fruit, flowers, etc.

A "reproductive unit" of a plant is any totipotent part or tissue of the plant from which one can obtain a progeny of the plant, including, for example, seeds, cuttings, buds, bulbs, somatic embryos, cultured cell (e.g., callus or suspension cultures), etc.

Nucleic Acids. Nucleic acids (a term used interchangeably with "polynucleotides" herein) that are useful in the practice of the present invention include the isolated taxadiene synthase gene, its homologs in other plant species, and fragments and variants thereof.

The term "taxadiene synthase gene" refers to a nucleic acid that contains a taxa-4(5),11(12)-diene synthase sequence, preferably a nucleic acid that encodes a polypeptide having taxadiene synthase enzymatic activity. This term relates primarily to the isolated full-length taxadiene synthase cDNA from Pacific yew discussed above and shown in FIG. 2 (SEQ ID NO: 1) and the corresponding genomic sequence (including flanking or internal sequences operably linked thereto, including regulatory elements and/or intron sequences).

This term also encompasses alleles of the taxadiene synthase gene from Pacific yew.

"Native". The term "native" refers to a naturally-occurring ("wild-type") nucleic acid or polypeptide.

"Homolog". A "homolog" of the taxadiene synthase gene is a gene sequence encoding a taxadiene synthase isolated from an organism other than Pacific yew.

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Fragments, probes, and primers. A fragment of a taxadiene synthase nucleic acid according to the present invention is a portion of the nucleic acid that is less than full-length and comprises at least a minimum length capable of hybridizing specifically with the taxadiene synthase nucleic acid of FIG. 2 (SEQ ID NO: 1) under stringent hybridization conditions. The length of such a fragment is preferably 15–17 nucleotides or more.

Nucleic acid probes and primers can be prepared based on the taxadiene synthase gene sequence provided in (SEQ ID NO: 1). A "probe" is an isolated DNA or RNA attached to a detectable label or reporter molecule, e.g., a radioactive isotope, ligand, chemiluminescent agent, or enzyme. "Primers" are isolated nucleic acids, generally DNA oligonucleotides 15 nucleotides or more in length, that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Methods for preparing and using probes and primers are described, for example, in Sambrook et al., *Molecular Cloning: A Laboratory Manual,* 2nd ed., vol. 1–3, ed. Sambrook et al., Cold Spring Harbor Laboratory Press, Cold Spring Harbor, N.Y., 1989; *Current Protocols in Molecular Biology,* ed. Ausubel et al., Greene Publishing and Wiley-Interscience, New York, 1987 (with periodic updates); and Innis et al., *PCR Protocols: A Guide to Methods and Applications,* Academic Press: San Diego, 1990. PCR-primer pairs can be derived from a known sequence, for example, by using computer programs intended for that purpose such as Primer (Version 0.5, ©1991, Whitehead Institute for Biomedical Research, Cambridge, Mass.).

Nucleotide sequence similarity. Nucleotide sequence "similarity" is a measure of the degree to which two polynucleotide sequences have identical nucleotide bases at corresponding positions in their sequence when optimally aligned (with appropriate nucleotide insertions or deletions). Sequence similarity can be determined using sequence analysis software such as the Sequence Analysis Software Package of the Genetics Computer Group, University of Wisconsin Biotechnology Center, Madison, Wis. Preferably, a variant form of a taxadiene synthase polynucleotide has at least 70%, more preferably at least 80%, and most preferably at least 90% nucleotide sequence similarity with a native taxadiene synthase gene, particularly with a native Pacific yew taxadiene synthase, as provided in (SEQ ID NO: 1).

Operably linked. A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is an isolated polypeptide made by an artificial combination of two otherwise separated segments of sequence, e.g., by chemical synthesis or by the manipulation of isolated segments of nucleic acids by genetic engineering techniques.

Techniques for nucleic-acid manipulation are described generally in, for example, Sambrook et al. (1989) and Ausubel et al. (1987, with periodic updates). Methods for chemical synthesis of nucleic acids are discussed, for example, in Beaucage and Carruthers, *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic Acids; Vectors, Transformation, Host Cells. Natural or synthetic nucleic acids according to the present invention can be incorporated into recombinant nucleic-acid constructs, typically DNA constructs, capable of introduction into and replication in a host cell. Such a construct preferably is a vector that includes a replication system and sequences that are capable of transcription and translation of a polypeptide-encoding sequence in a given host cell. For the practice of the present invention, conventional compositions and methods for preparing and using vectors and host cells are employed, as discussed, inter alla, in Sambrook et al., 1989, or Ausubel et al., 1987.

A "transformed" or "transgenic" cell, tissue, organ, or organism is one into which a foreign nucleic acid, has been introduced. A "transgenic" or "transformed" cell or organism also includes (1) progeny of the cell or organism and (2) progeny produced from a breeding program employing a "transgenic" plant as a parent in a cross and exhibiting an altered phenotype resulting from the presence of the "transgene," i.e., the recombinant taxadiene synthase nucleic acid.

Nucleic-Acid Hybridization; "Stringent Conditions"; "Specific". The nucleic-acid probes and primers of the present invention hybridize under stringent conditions to a target DNA sequence, e.g., to the taxadiene synthase gene.

The term "stringent conditions" is functionally defined with regard to the hybridization of a nucleic-acid probe to a target nucleic acid (i.e., to a particular nucleic-acid sequence of interest) by the hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968.

Regarding the amplification of a target nucleic-acid sequence (e.g., by PCR) using a particular amplification primer pair, stringent conditions are conditions that permit the primer pair to hybridize only to the target nucleic-acid sequence to which a primer having the corresponding wild-type sequence (or its complement) would bind and preferably to produce a unique amplification product.

The term "specific for (a target sequence)" indicates that a probe or primer hybridizes under stringent conditions only to the target sequence in a sample comprising the target sequence.

Nucleic-acid amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications,* Innis et al., eds., Academic Press, San Diego, 1990.

Methods of making cDNA clones encoding taxadiene synthase or homologs thereof. Based upon the availability of the taxadiene synthase cDNA as disclosed herein, other taxadiene synthase genes (e.g., alleles and homologs of taxadiene synthase) can be readily obtained from a wide variety of plants by cloning methods known in the art.

One or more primer pairs based on the taxadiene synthase sequence can be used to amplify such taxadiene synthase genes or their homologs by the polymerase chain reaction (PCR) or other conventional amplification methods. Alternatively, the disclosed taxadiene synthase cDNA or fragments thereof can be used to probe a cDNA or genomic library made from a given plant species by conventional methods.

Cloning of the taxadiene synthase genomic sequence and homologs Thereof. The availability of the taxadiene synthase cDNA sequence enables those skilled in the art to obtain a genomic clone corresponding to the taxadiene synthase cDNA (including the promoter and other regulatory regions and intron sequences) and the determination of its nucleotide sequence by conventional methods.

Virtually all Taxus species synthesize taxoids, including Taxol, to some degree (see, e.g., Mattina and Palva, *J. Environ. Hort.* 10:187–191, 1992; Miller, *J. Natural Products* 43:425–437, 1980). Any organism that produces taxoids would be expected to express a homolog of taxadiene synthase. Taxadiene synthase genes can be obtained by hybridization of a Pacific yew taxadiene synthase probe to a cDNA or genomic library of a target species. Such a homolog can also be obtained by PCR or other amplification method from genomic DNA or RNA of a target species using primers based on the taxadiene synthase sequence shown in (SEQ ID NO: 1). Genomic and cDNA libraries from yew or other plant species can be prepared by conventional methods.

Primers and probes based on the sequence shown in FIG. 2 can be used to confirm (and, if necessary, to correct) the taxadiene synthase sequence by conventional methods.

Nucleotide-Sequence Variants of taxadiene synthase cDNA and Amino Acid Sequence Variants of taxadiene synthase Protein. Using the nucleotide (SEQ ID NO: 1) and the amino-acid sequence (SEQ ID NO: 2) of the taxadiene synthase protein disclosed herein, those skilled in the art can create DNA molecules and polypeptides that have minor variations in their nucleotide or amino acid sequence.

"Variant" DNA molecules are DNA molecules containing minor changes in the native taxadiene synthase sequence, i.e., changes in which one or more nucleotides of a native taxadiene synthase sequence is deleted, added, and/or substituted, preferably while substantially maintaining taxadiene synthase activity. Variant DNA molecules can be produced, for example, by standard DNA mutagenesis techniques or by chemically synthesizing the variant DNA molecule or a portion thereof. Such variants preferably do not change the reading frame of the protein-coding region of the nucleic acid and preferably encode a protein having no change, only a minor reduction, or an increase in taxadiene synthase biological function.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant nucleic acids according to the present invention are "silent" or "conservative" variants. "Silent" variants are variants of a native taxadiene synthase sequence or a homolog thereof in which there has been a substitution of one or more base pairs but no change in the amino-acid sequence of the polypeptide encoded by the sequence. "Conservative" variants are variants of the native taxadiene synthase sequence or a homolog thereof in which at least one codon in the protein-coding region of the gene has been changed, resulting in a conservative change in one or more amino acid residues of the polypeptide encoded by the nucleic-acid sequence, i.e., an amino acid substitution. A number of conservative amino acid substitutions are listed below. In addition, one or more codons encoding cysteine residues can be substituted for, resulting in a loss of a cysteine residue and affecting disulfide linkages in the taxadiene synthase polypeptide.

| Original Residue | Conservative Substitution |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The taxadiene synthase gene sequence can be modified as follows:

(1) To improve expression efficiency and redirect the targeting of the expressed polypeptide: For expression in non-plant hosts (or to direct the expressed polypeptide to a different intracellular compartment in a plant host), the native gene sequence can be truncated from the 5' end to remove the sequence encoding the plastidial transit peptide of approximately 137 amino acids (ie., to approximately 138S), leaving the sequence encoding the mature taxadiene synthase polypeptide of about 725 amino acids. In addition, one or more codons can be changed, for example, to conform the gene to the codon usage bias of the host cell for improved expression. Enzymatic stability can be altered by removing or adding one or more cysteine residues, thus removing or adding one or more disulfide bonds.

(2) To alter catalytic efficiency: As discussed below, the aspartate-rich (I,L,V)XDDXX(XX)D motif(s) (SEQ ID NO: 6) found in most prenyltransferases and terpenoid cyclases, and thought to play a role in substrate binding, is also present in taxadiene synthase, as is a related DXXDD motif (FIG. 2, SEQ ID NO: 1 and SEQ ID NO: 4). Histidine and cysteine residues have been implicated at the active sites of several terpenoid cyclases of plant origin. Histidines residues 370, 415 and 793 and cysteines at residues 329, 650 and 777 of taxadiene synthase are conserved among the plant terpenoid cyclase genes.

One or more conserved histidine and cysteine residues (as discussed below), or semi-conserved residues such as conserved cysteine residues (e.g., residues 329, 650, 719, and 777) and histidine residues (e.g., residues 370, 415, 579, and 793), can be mutagenized to alter enzyme kinetics. In addition, residues adjacent to these conserved histidine and cysteine residues can also be altered to increase the cysteine or histidine content to improve charge stabilization. By increasing the aspartate content of the DDXXD and DXXDD motifs (SEQ ID NO: 3 and SEQ ID NO: 4, respectively) (where D is aspartate and X is any amino acid), which are likely to be involved in substrate/intermediate binding, it is also possible to increase the enzymatic rate (i.e., the rate-limiting ionization step of the enzymatic reaction). Arginines have been implicated in binding or catalysis, and conserved arginine residues are also good targets for mutagenesis. Changing the conserved DDXXD and/or DXXDD motifs (SEQ ID NO: 3 and SEQ ID NO: 4, respectively) (e.g., the aspartate residues thereof) by conventional site-directed mutagenesis methods to match those of other known enzymes can also lead to changes in the kinetics or substrate specificity of taxadiene synthase. Additionally, product formation can be altered by mutagenesis of the RWWK element (residues 564 to 567 (SEQ ID NO: 5)), which includes aromatic residues that may play a role in stabilizing carbocationic reaction intermediates.

(3) To modify substrate utilization: The enzyme, particularly the active site, can be modified to allow the enzyme to bind shorter (e.g., $C_{10}$) or longer (e.g., $C_{25}$) chains than geranylgeranyl diphosphate. Substrate size utilization can be altered by increasing or decreasing the size of the hydrophobic patches to modify the size of the hydrophobic pocket of the enzyme. Similar effects can be achieved by domain swapping.

(4) To change product outcome: Directed mutagenesis of conserved aspartate and arginine residues can be used to permit the enzyme to produce different diterpene skeletons with, for example, one, two, or three rings.

See, e.g., Cane et al., *Biochemistry* 34:2480–2488, 1995; Joly and Edwards, *J. Biol. Chem.* 268:26983–26989, 1993; Marrero et al., *J. Biol. Chem.* 267:533–536, 1992; and Song and Poulter, *Proc. Natl. Acad. Sci. USA* 91:3044–3048, 1994).

Expression of taxadiene synthase nucleic acids in host cells. DNA constructs incorporating a taxadiene synthase gene or fragment thereof according to the present invention preferably place the taxadiene synthase protein coding sequence under the control of an operably linked promoter that is capable of expression in a host cell. Various promoters suitable for expression of heterologous genes in plant cells are known in the art, including constitutive promoters, e.g. the cauliflower mosaic virus (CaMV) 35S promoter, which is expressed in many plant tissues, organ- or tissue-specific promoters, and promoters that are inducible by chemicals such as methyl jasminate, salicylic acid, or safeners, for example. A variety of other promoters or other sequences useful in constructing expression vectors are available for expression in bacterial, yeast, mammalian, insect, amphibian, avian, or other host cells.

Nucleic acids attached to a solid support. The nucleic acids of the present invention can be free in solution or attached by conventional means to a solid support, such as a hybridization membrane (e.g., nitrocellulose or nylon), a bead, or other solid supports known in the art.

Polypeptides

The term "taxadiene synthase protein" (or polypeptide) refers to a protein encoded by a taxadiene synthase gene, including alleles, homologs, and variants thereof, for example. A taxadiene synthase polypeptide can be produced by the expression of a recombinant taxadiene synthase nucleic acid or be chemically synthesized. Techniques for chemical synthesis of polypeptides are described, for example, in Merrifield, *J. Amer. Chem. Soc.* 85:2149–2156, 1963.

Polypeptide sequence identity and similarity. Ordinarily, taxadiene synthase polypeptides encompassed by the present invention have at least about 70% amino acid sequence "identity" (or homology) compared with a native taxadiene synthase polypeptide, preferably at least about 80% identity, and more preferably at least about 90% identity to a native taxadiene synthase polypeptide. Preferably, such polypeptides also possess characteristic structural features and biological activity of a native taxadiene synthase polypeptide.

Amino acid sequence "similarity" is a measure of the degree to which aligned amino acid sequences possess identical amino acids or conservative amino acid substitutions at corresponding positions.

A taxadiene synthase "biological activity" includes taxadiene synthase enzymatic activity as determined by conventional protocols (e.g., the protocol described in Hezari et al., *Arch. Biochem. Biophys.* 322:437–444, 1995, incorporated herein by reference). Other biological activities of taxadiene synthase include, but are not limited to substrate binding, immunological activity (including the capacity to elicit the production of antibodies that are specific for taxadiene synthase), etc.

Polypeptide identity (homology) or similarity is typically analyzed using sequence analysis software such as the Sequence Analysis Software Package of the Genetics Computer Group, University of Wisconsin Biotechnology Center, Madison, Wis.). Polypeptide sequence analysis software matches polypeptide sequences using measures of identity assigned to various substitutions, deletions, substitutions, and other modifications.

"Isolated," "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide which is chemically synthesized, or recombinant (i.e., the product of the expression of a recombinant nucleic acid, even if expressed in a homologous cell type) is considered to be isolated. A monomeric polypeptide is isolated when at least 60–90% by weight of a sample is composed of the polypeptide, preferably 95% or more, and more preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein purification. The polypeptides of the present invention can be purified by any of the means known in the art. Various methods of protein purification are described, e.g., in *Guide to Protein Purification,* ed. Deutscher, *Meth. Enzymol.* 185, Academic Press, San Diego, 1990; and Scopes, *Protein Purification: Principles and Practice,* Springer Verlag, N.Y., 1982.

Variant forms of taxadiene synthase polypeptides; labeling. Encompassed by the taxadiene synthase polypeptides according to an embodiment of the present invention are variant polypeptides in which there have been substitutions, deletions, insertions or other modifications of a native taxadiene synthase polypeptide. The variants substantially retain structural and/or biological characteristics and are preferably silent or conservative substitutions of one or a small number of contiguous amino acid residues. Preferably, such variant polypeptides are at least 70%, more preferably at least 80%, and most preferably at least 90% homologous to a native taxadiene synthase polypeptide.

The native taxadiene synthase polypeptide sequence can be modified by conventional methods, e.g., by acetylation, carboxylation, phosphorylation, glycosylation, ubiquitination, and labeling, whether accomplished by in vivo or in vitro enzymatic treatment of a taxadiene synthase polypeptide or by the synthesis of a taxadiene synthase polypeptide using modified amino acids.

There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al. (1989) and Ausubel et al. (1987 with periodic updates).

Polypeptide Fragments. The present invention also encompasses fragments of taxadiene synthase polypeptides that lack at least one residue of a native full-length taxadiene synthase polypeptide yet retain at least one of the biological activities characteristic of taxadiene synthase, e.g., taxadiene synthase enzymatic activity or possession of a characteristic immunological determinant. As an additional example, an immunologically active fragment of a taxadiene synthase polypeptide is capable of raising taxadiene synthase-specific antibodies in a target immune system (e.g., murine or rabbit) or of competing with taxadiene synthase for binding to taxadiene synthase-specific antibodies, and is thus useful in immunoassays for the presence of taxadiene synthase polypeptides in a biological sample. Such immunologically active fragments typically have a minimum size of 7 to 17 amino acids. Fragments preferably comprise at least 10, more preferably at least 20, and most preferably at least 30 consecutive amino acids of a native taxadiene synthase polypeptide.

Fusion polypeptides. The present invention also provides fusion polypeptides including, for example, heterologous fusion polypeptides, i.e., a taxadiene synthase polypeptide sequence or fragment thereof and a heterologous polypeptide sequence, e.g., a sequence from a different polypeptide. Such heterologous fusion polypeptides thus exhibit biological properties (such as ligand-binding, catalysis, secretion signals, antigenic determinants, etc.) derived from each of the fused sequences. Fusion partners include, for example, immunoglobulins, beta galactosidase, trpE, protein A, beta lactamase, alpha amylase, alcohol dehydrogenase, yeast alpha mating factor, and various signal and leader sequences which, e.g., can direct the secretion of the polypeptide. Fusion polypeptides are typically made by the expression of recombinant nucleic acids or by chemical synthesis.

Polypeptide sequence determination. The sequence of a polypeptide of the present invention can be determined by various methods known in the art. In order to determine the sequence of a polypeptide, the polypeptide is typically fragmented, the fragments separated, and the sequence of each fragment determined. To obtain fragments of a taxadiene synthase polypeptide, the polypeptide can be digested with an enzyme such as trypsin, clostripain, or Staphylococcus protease, or with chemical agents such as cyanogen bromide, o-iodosobenzoate, hydroxylamine or 2-nitro-5-thiocyanobenzoate. Peptide fragments can be separated, e.g., by reversed-phase high-performance liquid chromatography (HPLC) and analyzed by gas-phase sequencing.

Antibodies

The present invention also encompasses polygonal and/or monoclonal antibodies that are specific for taxadiene synthase, i.e., bind to taxadiene synthase and are capable of distinguishing the taxadiene synthase polypeptide from other polypeptides under standard conditions. Such antibodies are produced and assayed by conventional methods.

For the preparation and use of antibodies according to the present invention, including various immunoassay techniques and applications, see, e.g., Goding, *Monoclonal Antibodies: Principles and Practice,* 2d ed, Academic Press, New York, 1986; and Harlow and Lane, *Antibodies: A Laboratory Manual,* Cold Spring Harbor Laboratory, Cold Spring Harbor, N.Y., 1988. Taxadiene synthase-specific antibodies are useful, for example in: purifying taxadiene synthase polypeptides; cloning taxadiene synthase homologs from Pacific yew or other plant species from an expression library; antibody probes for protein blots and immunoassays; etc.

Taxadiene synthase polypeptides and antibodies can be labeled by conventional techniques. Suitable labels include radionuclides, enzymes, substrates, cofactors, inhibitors, fluorescent agents, chemiluminescent agents, magnetic particles, etc.

Plant transformation and regeneration. Any well-known method can be employed for plant cell transformation, culture, and regeneration can be employed in the practice of the present invention. Methods for introduction of foreign DNA into plant cells include, but are not limited to: transfer involving the use of *Agrobacterium tumefaciens* and appropriate Ti vectors, including binary vectors; chemically induced transfer (e.g., with polyethylene glycol); biolistics; and microinjection. See, e.g., An et al., *Plant Molecular Biology Manual* A3:1–19, 1988.

The invention will be better understood by reference to the following Examples, which are intended to merely illustrate the best mode now known for practicing the invention. The scope of the invention is not to be considered limited thereto, however.

EXAMPLE 1

Cloning and Sequencing of a cDNA encoding Taxa-4(5),11(12)-diene Synthase

Materials and Methods

Plants, Substrates, and Standards. Four-year-old *T. brevifolia* saplings in active growth were maintained in a greenhouse. [1–3H]Geranylgeranyl diphosphate (120 Ci/mol) was prepared as described previously (LaFever et al., *Arch. Biochem. Biophys.* 313:139–149, 1994), and authentic (±)-taxa-4(5),11(12)-diene was prepared by total synthesis (Rubenstein, *J. Org. Chem.* 60:7215–7223, 1995).

Library Construction. Total RNA was extracted from *T. brevifolia* stem using the procedures of Lewinsohn and associates (Lewinsohn et al., *Plant Mol. Biol. Rep.* 12:20–25, 1991) developed for woody gymnosperm tissue. Poly(A)+RNA was purified by chromatography on oligo (dT)-cellulose (Pharmacia) and 5 g of the resulting mRNA was utilized to construct a ZAP II cDNA library according to the manufacturer's instructions (Stratagene).

PCR-Based Probe Generation and Library Screening. Comparison of six available sequences for monoterpene, sesquiterpene, and diterpene cyclases from higher plants (Facchini and Chappell, *Proc. Natl. Acad. Sci. USA* 89:11088–11092, 1992; Colby et al., *J. Biol. Chem.* 268:23016–23024, 1993; Mau and West, *Proc. Natl. Acad. Sci. USA* 91:8497–8501, 1994; Back and Chappell, *J. Biol. Chem.* 270:7375–7381, 1995; Sun and Karmiya, *Plant Cell* 6:1509–1518, 1994; and Bensen et al., *Plant Cell* 7:75–84, 1995) allowed definition of eleven homologous regions for which consensus degenerate primers were synthesized. All twenty primers (the most carboxy terminal primer, the most amino terminal primer, and nine internal primers in both directions) were deployed in all possible combinations with a broad range of amplification conditions using CsCl-purified *T. brevifolia* stem library phage DNA as template (Innis and Gelfand, in *PCR Protocols* (Innis et al., eds), pp. 3–12, 253–258, Academic Press, San Diego, Calif., 1990; Sambrook et al., 1989).

Analysis of PCR products by gel electrophoresis (Sambrook et al., 1989) indicated that only the combination of primers CC7.2F and CC3R (see FIG. 2 and SEQ ID NO: 1) generated a specific DNA fragment (~80 bp). This DNA fragment was cloned into pT7Blue (Novagen) and sequenced (DyeDeoxy Terminator Cycle Sequencing, Applied Biosystems), and shown to be 83 bp in length. PCR was used to prepare approximately 1 g of this material for random hexamer labeling with [-32P]dATP (Tabor et al., in *Current Protocols in Molecular Biology,* Ausubel et al., Sections 3.5.9–3.5.10, 1987) and use as a hybridization probe to screen filter lifts of 3×105 plaques grown in *E. coli* LE392 using standard protocols (Britten and Davidson, in *Nucleic Acid Hybridisation,* Hames and Higgins, eds., pp. 3–14, IRL Press, Oxford, 1988).

Of the plaques affording positive signals (102 total), 50 were purified through two additional cycles of hybridization. Thirty-eight pure clones were in vivo excised as Bluescript phagemids. The insert size was determined by PCR using T3 and T7 promoter primers, and the twelve largest clones (insert >2 kb) were partially sequenced.

cDNA Expression in *E. coli*. All of the partially sequenced, full-length inserts were either out of frame or bore premature stop sites immediately upstream of the presumptive methionine start codon. The latter complication likely resulted from hairpin-primed second-strand cDNA synthesis (Old and Primrose, *Principles of Gene Manipulation,* 4th ed., pp. 3435, Blackwell Scientific, London, 1989). The 2.7-kb insert from pTb42 was cloned into frame by PCR using the thermostable, high fidelity, blunting polymerase Pful (Stratagene) and the FRM42 primer (downstream of false stop codons) and T7 promoter primer. The resulting blunt fragment was ligated into EcoRV-digested pBluescript SK(-) (Stratagene), yielding pTb42.1, and transformed into *E. coli* XL1-Blue (Stratagene).

To evaluate functional expression of terpene cyclase activity, *E. coli* XL1-Blue cells harboring pTb42.1 were grown (to A600=0.4) on 5 ml LB medium supplemented with 100 g/ml ampicillin and 12.5 g/ml tetracycline before induction with 200 M IPTG and subsequent growth for 4 h at 25° C. Bacteria were harvested by centrifugation (1800 g, 10 min), resuspended in taxadiene synthase assay buffer (Hezari et al., *Arch. Biochem. Biophys.* 322:437–444, 1995), disrupted by brief sonication at 0–4° C., and the resulting suspension centrifuged (18,000 g, 10 min) to pellet debris. The supernatant was assayed for taxadiene synthase activity by an established protocol (Hezari et al., *Arch. Biochem. Biophys.* 322:437–444, 1995) in the presence of 15 M [1–3H]geranylgeranyl diphosphate and 1 mM MgCl2, with incubation at 31° C. for 4 h. The reaction products were extracted with pentane and the extract purified by column chromatography on silica gel as previously described (Hezari et al., *Arch. Biochem. Biophys.* 322:437–444, 1995) to afford the olefin fraction, an aliquot of which was counted by liquid scintillation spectrometry to determine 3H incorporation. Control experiments with transformed *E. coli* bearing the plasmid with out-of-frame inserts were also carried out.

The identity of the olefin product of the recombinant enzyme was verified by capillary radio-gas chromatography ("capillary radio-GC") (Croteau and Satterwhite, *J. Chromatogr.* 500:349–354, 1990) as well as capillary gas chromatography-mass spectrum/spectrometry ("capillary GC-MS") using methods described previously (Koepp et al., *J. Biol. Chem.* 270:8686–8690, 1995) and authentic taxa-4 (5),11(12)-diene (Rubenstein, *J. Org. Chem.* 60:7215–7223, 1995). For GC-MS analysis (Hewlett-Packard 6890 GC-MSD), selected diagnostic ions were monitored: m/z 272 [P+]; 257 [P+–15(CH3)]; 229 [P+–43(C3H7)]; 121, 122, 123 [C-ring fragment cluster]; and 107 [m/z 122 base peak–15(CH3)]. The origin of the highly characteristic C-ring double cleavage fragment ion [base peak, m/z 122 (C9H14)] has been described (Koepp et al., *J. Biol. Chem.* 270:8686–8690, 1995).

RESULTS AND DISCUSSION cDNA Isolation and Characterization. In general characteristics (molecular weight, divalent metal ion requirement, kinetic constants, etc.), taxadiene synthase resembles other terpenoid cyclases from higher plants; however, the low tissue titers of the enzyme and its instability under a broad range of fractionating conditions impeded purification of the protein to homogeneity (Hezari et al., *Arch. Biochem. Biophys.* 322:437–444, 1995). A 10 g sample of the electrophoretically-purified cyclase, prepared by standard analytical procedures (Schagger and von Jagow, *Anal. Biochem.* 166:368–379, 1987; Towbin et al., *Proc. Natl. Acad. Sci. USA* 76:350–4354, 1979), failed to provide amino-terminal sequence via Edman degradation. Repeated attempts at trypsinization and CNBr cleavage of comparable protein samples also failed to provide sequenceable peptides, in large part because of very low recoveries.

As an alternate approach to cDNA library screening using protein-based oligonucleotide probes, a PCR-based strategy was developed that was founded on a set of degenerate primers for PCR amplification designed to recognize highly-conserved regions of six higher plant terpene cyclases whose nucleotide sequences are known. Three of these cyclases, (−)-limonene synthase (a monoterpene cyclase from spearmint) (Colby et al., *J. Biol. Chem.* 268:23016–23024, 1993), epi-aristolochene synthase (a sesquiterpene cyclase from tobacco) (Facchini and Chappell, *Proc. Natl. Acad. Sci. USA* 89:11088–11092, 1992; Back and Chappell, *J. Biol. Chem.* 270:7375–7381, 1995), and casbene synthase (a diterpene cyclase from castor bean) (Mau and West, *Proc. Natl. Acad. Sci. USA* 91:8497–8501, 1994), exploit reaction mechanisms similar to taxadiene synthase in the cyclization of the respective geranyl (C10), farnesyl (C15), and geranylgeranyl (C20) diphosphate substrates (Lin et al., *Biochemistry*, in press). Kaurene synthase A from *Arabidopsis thaliana* (Sun and Karmiya, *Plant Cell* 6:1509–1518, 1994) and maize (Bensen et al., *Plant Cell* 7:75–84, 1995) and (−)-abietadiene synthase from grand fir (*Abies grandis*; Stofer Vogel, Wildung, Vogel, and Croteau, manuscript in preparation) exploit a quite different mechanism that involves protonation of the terminal double bond of geranylgeranyl diphosphate to initiate cyclization to the intermediate copalyl diphosphate followed, in the case of abietadiene synthase, by the more typical ionization of the diphosphate ester function to initiate a second cyclization sequence to the product olefin (LaFever et al., *Arch. Biochem. Biophys.* 313:139–149, 1994). The latter represents the only gymnosperm terpene cyclase sequence presently available.

Comparison of deduced amino acid sequences between all of the cyclases targeted eleven regions for PCR primer construction. Testing of all twenty primers in all combinations under a broad range of amplification conditions, followed by product analysis by gel electrophoresis, revealed that only one combination of primers [CC7.2 (forward) with CC3 (reverse), see FIG. 2 for locations] yielded a specific DNA fragment (83 bp) using *T. brevifolia* library phage as template. Primer CC3 delineates a region of strong homology between (−)-limonene synthase (Colby et al., *J. Biol. Chem.* 268:23016–23024, 1993), epi-aristolochene synthase (Facchini and Chappell, *Proc. Natl. Acad. Sci. USA* 89:11088–11092, 1992) and casbene synthase (Mau and West, *Proc. Natl. Acad. Sci. USA* 91:8497–8501, 1994). Primer CC7.2 was selected based on sequence comparison of the angiosperm diterpene cyclases (Mau and West, *Proc. Natl. Acad. Sci. USA* 91:8497–8501, 1994; Sun and Karmiya, *Plant Cell* 6:1509–1518, 1994; Bensen et al., *Plant Cell* 7:75–84, 1995) to the recently acquired cDNA clone encoding a gymnosperm diterpene cyclase, (−)-abietadiene synthase from grand fir (Stofer Vogel, Wildung, Vogel, and Croteau, manuscript in preparation).

The 83 bp fragment was cloned and sequenced, and thus demonstrated to be cyclase-like. This PCR product was 32P-labeled for use as a hybridization probe and employed in high stringency screening of 3×105 plaques which yielded 102 positive signals. Fifty of these clones were purified through two additional rounds of screening, in vivo excised and the inserts sized. The twelve clones bearing the largest inserts (>2.0 kb) were partially sequenced, indicating that they were all representations of the same gene. Four of these inserts appeared to be full-length.

cDNA Expression in *E. coli*. All four of the full-length clones that were purified were out of frame or had stop sites immediately upstream of the starting methionine codon resulting from hairpin-primed second strand cDNA synthesis. The insert from pTb42 was cloned into frame by PCR methods, the blunt fragment was ligated into the EcoRV-site of pBluescript SK(−), yielding pTb42. 1, and transformed into *E. coli* XL1 -Blue.

Transformed *E. coli* were grown in LB medium supplemented with antibiotics and induced with IPTG. The cells were harvested and homogenized, and the extracts were assayed for taxadiene synthase activity using standard protocols with [1–3H]geranylgeranyl diphosphate as substrate (Hezari et al., *Arch. Biochem. Biophys.* 322:437–444, 1995). The olefin fraction isolated from the reaction mixture contained a radioactive product (~1 nmol) that was coincident on capillary radio-GC with authentic taxa-5(5),11(12)-diene (Rt=19.40±0.13 min).

The identification of this diterpene olefin was confirmed by capillary GC-MS analysis. The retention time (12.73 min. vs. 12.72 min.) and selected ion mass spectrum (Table I) of the diterpene olefin product was identical to that of authentic (±)-taxa-4(5),11 (12)-diene (Rubenstein, *J. Org. Chem.* 60:7215–7223, 1995). The origin of the selected diagnostic ions shown in Table I, which account for most of full spectrum abundance, are described herein and elsewhere (Koepp et al., *J. Biol. Chem.* 270:8686–8690, 1995). Because of different sample sizes, the total abundance of the authentic standard (2.96 E5) was approximately twice that of the biosynthetic olefin (1.42 E5). This, and variation in background between runs, probably account for minor differences in relative abundances of the high mass fragments.

TABLE 1

GC-MS Analysis of the Diterpene Olefin Synthesized by Recombinant Taxadiene Synthase ("Product") Compared to Authentic Taxa-4(5), 11(12)-diene ("Standard")

| | Relative Abundance | |
|---|---|---|
| m/z | Product | Standard |
| 107 | 153 | 15.3 |
| 121 | 14.3 | 14.3 |
| 122 | 58.1 | 58.7 |
| 123 | 10.2 | 10.3 |
| 229 | 0.56 | 0.71 |
| 257 | 0.35 | 0.45 |
| 272 | 1.19 | 1.17 |

Since identically prepared extracts of control cultures of *E. coli* that were transformed with pBluescript bearing an out-of-frame insert were incapable of transforming geranylgeranyl diphosphate to detectable levels of diterpene olefin, these results confirm that clone pTb42.1 encodes the taxadiene synthase from Pacific yew.

Sequence Analysis. Both strands of the inserts from pTb42 and pTb42.1 were sequenced. No mistakes were incorporated by Pfu polymerase. The pTb42.1 taxadiene synthase cDNA is 2700 nucleotides in length and contains a complete open reading frame of 2586 nucleotides (FIG. 2 and SEQ ID NO: 1). The deduced amino acid sequence (SEQ ID NO: 1 and SEQ ID NO: 2) indicates the presence of a putative plastidial transit peptide of approximately 137 amino acids and a mature protein of about 725 residues (~82.5 kDa), based on the size of the native (mature) enzyme (~79 kDa) as estimated by gel permeation chromatography and sodium dodecyl sulfate-polyacrylamide gel electrophoresis ("SDS-PAGE") (Hezari et al., *Arch. Biochem. Biophys.* 322:437–444, 1995), the characteristic amino acid content and structural features of such aminoterminal targeting sequences, and their cleavage sites (Keegstra et al., *Annu. Rev. Plant Physiol. Plant Mol. Biol.* 40:471–501, 1989; von Heijne et al., *Eur. J. Biochem.* 180:535–545, 1989), and the fact that diterpene biosynthesis is localized exclusively within plastids (West et al., *Rec. Adv. Phytochem.* 13:163–198, 1979; Kleinig, *Annu. Rev. Plant Physiol. Plant Mol. Biol.* 40:39–59, 1989). The transit peptide/mature protein junction and thus the exact lengths of both moieties are unknown, because the amino terminus of the mature protein is apparently blocked and has not yet been identified.

Pairwise sequence comparison (Feng and Doolittle, *Methods Enzymol.* 183:375–387, 1990; Genetics Computer Group, *Program Manual for the Wisconsin Packet, Version 8*, Genetics Computer Group, Madison, Wis., 1994) with other terpene cyclases from higher plants revealed a significant degree of sequence similarity at the amino acid level. The taxadiene synthase from yew showed 32% identity and 55% similarity to (−)-limonene synthase from spearmint (Colby et al., *J. Biol. Chem.* 268:23016–23024, 1993), 30% identity and 54% similarity to epi-aristolochene synthase from tobacco (Facchini and Chappell, *Proc. Natl. Acad. Sci. USA* 89:11088–11092, 1992), 31% identity and 56% similarity to casbene synthase from castor bean (Mau and West, *Proc. Natl. Acad. Sci. USA* 91:8497–8501, 1994), and 33% identity and 56% similarity to kaurene synthase A from *Arabidopsis thaliana* and maize (Sun and Karmiya, *Plant Cell* 6:1509–1518, 1994; Bensen et al., *Plant Cell* 7:75–84, 1995), and 45% identity and 67% similarity to (−)-abietadiene synthase from grand fir (Stofer Vogel, Wildung, Vogel, and Croteau, manuscript in preparation). Pairwise comparison of other members within this group show roughly comparable levels of identity (30–40%) and similarity (50–60%). These terpenoid synthases represent a broad range of cyclase types from diverse plant families, supporting the suggestion of a common ancestry for this class of enzymes (Colby et al., *J. Biol. Chem.* 268:23016–23024, 1993; Mau and West, *Proc. Natl. Acad. Sci. USA* 91:8497–8501, 1994; Back and Chappell, *J. Biol. Chem.* 270:7375–7381, 1995; McGarvey and Croteau, *Plant Cell* 7:1015–1026, 1995; Chappell, *Annu. Rev. Plant Physiol. Plant Mol. Biol.* 46:521–547, 1995).

The amino acid sequence of taxadiene synthase (SEQ ID NO: 1 and SEQ ID NO: 2) does not closely resemble (identity ~20%; similarity ~40%) that of any of the microbial sesquiterpene cyclases that have been determined recently (Hohn and Beremand, *Gene (Amst.)* 79:131–136, 1989; Proctor and Hohn, *J. Biol. Chem.* 268:4543–4548, 1993; Cane et al., *Biochemistry* 33:5846–5857, 1994), nor does the taxadiene synthase sequence resemble any of the published sequences for prenyltransferases (Chen et al., *Protein Sci.* 3:600–607, 1994; Scolnik and Bartley, *Plant Physiol.* 104:1469–1470, 1994; Attucci et al. *Arch. Biochem. Biophys.* 321:493–500, 1995), a group of enzymes that, like the terpenoid cyclases, employ allylic diphosphate substrates and exploit similar electrophilic reaction mechanisms (Poulter and Rilling, in *Biosynthesis of Isoprenoid Compounds,* Porter and Spurgeon, eds., vol. 1, pp. 161–224, Wiley & Sons, New York, N.Y., 1981). The aspartate-rich (I,L,V)XDDXX(XX)D motif(s) (SEQ ID NO: 6) found in most prenyltransferases and terpenoid cyclases (Facchini and Chappell, *Proc. Natl. Acad. Sci. USA* 89:11088–11092, 1992; Colby et al., *J. Biol. Chem.* 268:23016–23024, 1993; Mau and West, *Proc. Natl. Acad. Sci. USA* 91:8497–8501, 1994; Back and Chappell, *J. Biol. Chem.* 270:7375–7381, 1995; Hohn and Beremand, *Gene (Amst.)* 79:131–136, 1989; Proctor and Hohn, *J. Biol. Chem.* 268:4543–4548, 1993; Cane et al., *Biochemistry* 33:5846–5857, 1994; Chen et al., *Protein Sci.* 3:600–607, 1994; Scolnik and Bartley, *Plant Physiol.* 104:1469–1470, 1994; Attucci et al. *Arch. Biochem. Biophys.* 321:493–500, 1995; Abe and Prestwich, *J. Biol. Chem.* 269:802–804, 1994), and thought to play a role in substrate binding (Chen et al., *Protein Sci.* 3:600–607, 1994; Abe and Prestwich, *J. Biol. Chem.* 269:802–804, 1994; Marrero et al., *J. Biol. Chem.* 267:21873–21878, 1992; Joly and Edwards, *J. Biol. Chem.* 268:26983–26989, 1993; Tarshis et al., *Biochemistry* 33:10871–10877, 1994), is also present in taxadiene synthase, as is a related DXXDD motif (FIG. 2 SEQ ID NO: 1 and SEQ ID NO: 4). Histidine and cysteine residues have been implicated at the active sites of several terpenoid cyclases of plant origin (Rajaonarivony et al., *Arch. Biochem. Biophys.* 299:77–82, 1992; Savage et al., *Arch. Bio-*

*chem. Biophys.* 320:257–265, 1995). A search of the aligned sequences revealed that three histidines (at positions 370, 415 and 793) and three cysteines (at positions 329, 650 and 777) of taxadiene synthase are conserved among the plant terpenoid cyclase genes. The taxadiene synthase from yew most closely resembles the abietadiene synthase from grand fir rather than the casbene synthase from castor bean (Mau and West, *Proc. Natl. Acad. Sci. USA* 91:8497–8501, 1994), which catalyzes a similar type of cyclization reaction but is phylogenetically quite distant. The abietadiene synthase from grand fir is the only other terpenoid cyclase sequence from a gymnosperm now available (Stofer Vogel, Wildung, Vogel, and Croteau, in preparation), and these two diterpene cyclases from the coniferales share several regions of significant sequence homology, one of which was fortuitously chosen for primer construction and proved to be instrumental in the acquisition of a PCR-derived probe that led to the cloning of taxadiene synthase.

EXAMPLE 3

Expression of Taxadiene Synthase Genes Truncated to Remove Transit Peptide Sequences The native taxadiene synthase gene sequence was truncated from the 5' end to removing part or all of the sequence that encodes the plastidial transit peptide of approximately 137 amino acids (the mature taxadiene synthase polypeptide is about 725 amino acids.) Deletion mutants were produced that remove amino acid residues from the amino terminus up to residue 31 (Glu), 39 (Ser), 49 (Ser), 54 (Gly), 79 (Val), or 82 (Ile). These mutants were expressed in *E. coli* calls and cell extracts were assayed for taxadiene synthase activity as described above. In preliminary experiments, expression of truncation mutants up was increased over wild-type taxadiene synthase by up to about 50%, with further truncation past residues 83–84 apparently decreasing taxadiene synthase activity.

Truncation of at least part of the plastidial transit peptide improves taxadiene synthase expression. Moreover, removing this sequence improves purification of taxadiene synthase, since the transit peptide is recognized by *E. coli* chaperonins, which co-purify with the enzyme and complicate purification, and because the taxadiene synthase preprotein tends to form inclusion bodies when expressed in *E. coli*.

The actual cleavage site for removal of the transit peptide may not be at the predicted cleavage site between residue 136 (Ser) and residue 137 (Pro). A transit peptide of 136 residues appears quite long, and other (monoterpene) synthases have a tandem pair of arginines (Arg-Arg) at about residue 60 (Met). Truncation immediately amino-terminal to the tandem pair of arginines of these synthases has resulted in excellent expression in *E. coli*. Taxadiene synthase lacks an Arg-Arg element. Also, truncation beyond residues 83–84 leads to lower activity.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

What is claimed is:

1. An isolated polynucleotide comprising a polypeptide-encoding sequence that encodes a polypeptide with taxadiene synthase biological activity, wherein the polypeptide-encoding sequence encodes a polypeptide comprising only conservative amino acid substitutions of the amino acid sequence shown in SEQ ID NO: 2.

2. The polynucleotide of claim 1 wherein the polypeptide-encoding sequence encodes a polypeptide comprising only conservative amino acid substitutions to the taxadiene synthase polypeptide sequence shown in SEQ ID NO: 2 except for an amino acid substitution at at least one location selected from the group consisting of: cysteine residues 329, 650, 719, and 777; histidine residues 370, 415, 579, and 793; a DDXXD (SEQ ID NO: 3) motif; a DXXDD (SEQ ID NO: 4) motif; a conserved arginine; and a RWWK (SEQ ID NO: 5) element.

3. The polynucleotide of claim 1 wherein the polypeptide-encoding sequence encodes a polypeptide that lacks at least part of a transit peptide sequence of the sequence shown in SEQ ID NO: 2.

4. A cell comprising the polynucleotide of claim 1.

5. A plant cell comprising the polynucleotide of claim 1.

6. A transgenic plant comprising the polynucleotide of claim 1.

7. A method of expressing a taxadiene synthase polypeptide in a cell, the method comprising the steps of:

providing a cell that comprises an expressible polynucleotide that encodes a taxadiene synthase polypeptide according to claim 3; and culturing the cell under conditions suitable for expression of the polypeptide.

8. The method of claim 7 wherein the cell is a taxoid-producing cell.

9. The method of claim 7 wherein expression of the polynucleotide causes the cell to produce a higher level of a taxoid than an otherwise similar cell that lacks the expressible polynucleotide.

* * * * *